US012465487B2

(12) United States Patent
Zhang

(10) Patent No.: US 12,465,487 B2
(45) Date of Patent: Nov. 11, 2025

(54) POLYMERIC HEART VALVE AND PREPARATION METHOD THEREFOR

(71) Applicant: SUZHOU HEARTHILL MEDICAL TECHNOLOGY CO., LTD., Jiangsu (CN)

(72) Inventor: Zhigang Zhang, Suzhou (CN)

(73) Assignee: SUZHOU HEARTHILL MEDICAL TECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 19/065,402

(22) Filed: Feb. 27, 2025

(65) Prior Publication Data

US 2025/0195216 A1 Jun. 19, 2025

Related U.S. Application Data

(63) Continuation of application No. PCT/CN2024/095085, filed on May 24, 2024.

(30) Foreign Application Priority Data

May 31, 2023 (CN) ......................... 202310630756.3

(51) Int. Cl.
*A61F 2/24* (2006.01)

(52) U.S. Cl.
CPC .......... *A61F 2/2418* (2013.01); *A61F 2/2415* (2013.01); *A61F 2230/0069* (2013.01); *A61F 2240/001* (2013.01)

(58) Field of Classification Search
CPC .... A61F 2/2415; A61F 2/2409; A61F 2/2418; A61F 2/24; A61F 2/2445
See application file for complete search history.

(56) References Cited

U.S. PATENT DOCUMENTS 4,364,127 A * 12/1982 Pierce .................... A61F 2/2409 137/849
4,506,394 A * 3/1985 Bedard ................. A61F 2/2412 623/2.38

(Continued)

FOREIGN PATENT DOCUMENTS

CN 115778635 B * 5/2023 ............... A61F 2/24
DE 102014223522 A1 * 5/2016 ........... A61F 2/2412

(Continued)

OTHER PUBLICATIONS

Chinese Notification of Grant of Invention Patent issued on Jan. 12, 2024, in corresponding Chinese Patent Application No. 202310630756.3. (2 pages English, 3 pages Chinese).

(Continued)

*Primary Examiner* — Seema Mathew
(74) *Attorney, Agent, or Firm* — NSIP Law

(57) ABSTRACT

Provided by the present invention are a polymeric heart valve and a preparation method therefor. The polymeric heart valve comprises valve leaflets and a valve frame. The valve frame is a hollow cylindrical structure and comprises a first end and a second end; the first end is provided with a plurality of column peaks arranged at intervals in the circumferential direction, and column valleys are correspondingly formed. The number of the valve leaflets is consistent with the number of the column peaks. The valve leaflets are arranged in the center of the first end. According to the polymeric heart valve provided by the present invention, the radial supporting force of the valve frame is increased by optimizing the structure and the process, thereby improving valve performance, simplifying the preparation process, and improving the preparation efficiency.

6 Claims, 5 Drawing Sheets

(56) References Cited

U.S. PATENT DOCUMENTS

| | | | | | |
|---|---|---|---|---|---|
| 4,705,516 | A * | 11/1987 | Barone | A61F 2/2409 | 623/2.39 |
| 4,888,009 | A * | 12/1989 | Lederman | A61F 2/2412 | 623/2.19 |
| 5,147,391 | A * | 9/1992 | Lane | A61F 2/2412 | 623/2.18 |
| 5,376,111 | A * | 12/1994 | Bokros | A61F 2/2403 | 623/2.3 |
| 5,562,729 | A * | 10/1996 | Purdy | A61F 2/2412 | 623/2.19 |
| 5,769,780 | A * | 6/1998 | Hata | A61F 2/2412 | 8/94.11 |
| 5,843,183 | A * | 12/1998 | Bokros | A61F 2/2403 | 623/2.22 |
| 6,174,331 | B1 * | 1/2001 | Moe | A61F 2/2412 | 623/901 |
| 6,953,332 | B1 * | 10/2005 | Kurk | B29C 41/14 | 264/303 |
| 7,871,435 | B2 * | 1/2011 | Carpentier | A61F 2/2418 | 623/2.14 |
| 8,986,374 | B2 * | 3/2015 | Cao | A61F 2/2409 | 623/2.18 |
| 11,826,248 | B2 * | 11/2023 | Bruchman | A61F 2/2415 | |
| 2003/0078652 | A1 * | 4/2003 | Sutherland | A61F 2/2412 | 623/2.12 |
| 2003/0114924 | A1 * | 6/2003 | Moe | A61F 2/2412 | 623/2.12 |
| 2005/0165479 | A1 * | 7/2005 | Drews | A61F 2/2412 | 623/2.38 |
| 2006/0195185 | A1 * | 8/2006 | Lane | A61F 2/2412 | 623/2.38 |
| 2007/0016289 | A1 * | 1/2007 | Johnson | A61F 2/2409 | 623/2.17 |
| 2007/0260305 | A1 * | 11/2007 | Drews | A61F 2/243 | 623/2.11 |
| 2011/0257738 | A1 * | 10/2011 | Corbett | A61F 2/2415 | 623/2.12 |
| 2011/0257739 | A1 * | 10/2011 | Corbett | A61F 2/2412 | 623/2.18 |
| 2014/0005772 | A1 * | 1/2014 | Edelman | A61L 27/34 | 29/890.12 |
| 2023/0042537 | A1 * | 2/2023 | Conklin | A61F 2/2412 | |
| 2023/0147758 | A1 * | 5/2023 | Drasler | A61F 2/2418 | 623/2.11 |
| 2025/0161031 | A1 * | 5/2025 | Jin | A61F 2/2409 | |

FOREIGN PATENT DOCUMENTS

| | | | | |
|---|---|---|---|---|
| EP | 3838222 | A1 * | 6/2021 | A61F 2/2418 |
| WO | WO-9404099 | A1 * | 3/1994 | A61F 2/2415 |
| WO | WO-2016078659 | A1 * | 5/2016 | A61F 2/2412 |
| WO | WO-2019089163 | A1 * | 5/2019 | A61L 27/16 |

OTHER PUBLICATIONS

International Searching Authority issued Written Opinion on Aug. 27, 2024, in corresponding International Application No. PCT/CN2024/095085. (5 pages in English, 5 pages in Chinese).

* cited by examiner

POLYMERIC HEART VALVE AND PREPARATION METHOD THEREFOR

CROSS-REFERENCE TO RELATED APPLICATIONS

This application claims priority to Chinese Patent Application No. 202310630756.3, filed on May 31, 2023, entitled "POLYMERIC HEART VALVE AND PREPARATION METHOD THEREFOR", which is incorporated herein by reference in its entirety.

TECHNICAL FIELD

The present invention relates to the field of medical devices, particularly to a polymeric heart valve and a preparation method therefor.

BACKGROUND ART

A heart valve is a valve between an atrium and a ventricle or between a ventricle and an artery. Valves play a crucial role in the never-ending blood circulation activity of the heart: acting as gatekeepers, preventing blood from flowing back to the newly left atrium or ventricle. A prosthetic heart valve is a cardiac implant interventional medical device for the treatment of heart valve disease or defect. The artificial heart was first applied in clinical practice in 1960 and has since gone through stages such as mechanical valves, biological tissue valves, and interventional valves. It has become a very important medical device in the field of cardiovascular therapy.

Patent CN 114126822 A discloses a heart valve, in order to improve the radial support force of the valve frame, the valve leaflets and the valve frame are made of materials with different hardnesses, and the valve frame and the valve leaflets are bonded together by means of high-temperature injection molding, etc. This method requires two injection moldings, increasing not only the amount of valve fabrication but also the risk of poor bonding between the valve frame and valve leaflets.

SUMMARY OF THE INVENTION

Embodiments of the present invention provide a polymeric heart valve and a preparation method therefor that optimizes valve performance by improving the radial support of the valve frame by means of optimizing the structure and process.

A polymeric heart valve provided by an embodiment of the present invention includes a valve leaflet and a valve frame. The valve frame is a hollow cylindrical structure and includes a first end and a second end. The first end is provided with a plurality of column peaks arranged at intervals in the circumferential direction, and column valleys are correspondingly formed. The number of the valve leaflets is consistent with the number of the column peaks. The valve leaflets are arranged in the center of the first end. A plurality of valve leaflets are sequentially connected to two adjacent column peaks in the circumferential direction. The valve further includes an insert. The insert is a hollow cylindrical structure matching the valve frame. The insert includes a third end and a fourth end corresponding to the first end and the second end, respectively. The insert is suitable for being embedded in the valve frame in the axial direction. The insert includes an axial positioning structure and a radial positioning structure. The valve leaflets and the valve frame are subjected to one-time injection molding, and the insert is embedded into the valve frame to become a whole when the valve frame and the valve leaflets are subjected to injection molding.

Optionally, the axial positioning structure includes positioning peaks arranged at the third end and corresponding to the column peaks in the circumferential direction. The positioning peak is symmetrically provided on both sides with positioning grooves and formed with positioning side peaks at edges of the positioning peak.

Optionally, the axial positioning structure further includes a plurality of sets of positioning teeth arranged at intervals. The positioning teeth are provided at the fourth end. The circumferential positions of the plurality of sets of the positioning teeth correspond to the column peaks and the column valleys on a one-to-one basis. Each set of positioning teeth includes two teeth.

Optionally, the radial positioning structure includes positioning protrusions arranged on the outer wall of the insert. The positioning protrusions are uniformly arranged on the outer wall of the insert.

Optionally, the center of the valve leaflets is provided with a gas-permeable groove having a diameter of 0.005 mm-0.01 mm.

Optionally, the insert is provided with a plurality of lightening holes. The plurality of lightening holes are arranged at intervals in a circumferential direction. The lightening holes are respectively arranged between adjacent column peaks and column valleys.

Optionally, the second end is provided with an annular edge.

Optionally, the material of the valve leaflets and the valve frame are made of a polymer material and the insert is made of a hard material.

In accordance with another aspect of the present invention, also provided is an injection mold for preparing the valve described above. The injection mold includes a mold cavity and a mold core. An outer wall of the mold core mates with an inner wall of the mold cavity to form an injection cavity. The insert is arranged in the injection cavity of the injection mold when the valve frame and the valve leaflet are subjected to one-time injection molding. The apexes of the positioning protrusions abut the inner wall of the mold cavity, making the distance between the outer wall of the insert and the inner wall of the mold cavity equal to the distance between the inner wall of the insert and the outer wall of the mold core.

Optionally, the mold cavity is provided with injection holes that are arranged in correspondence to the first end of the valve frame.

Optionally, the number of the injection holes is plural, and the plurality of the injection holes are provided in correspondence with the column peaks on a one-to-one basis.

In accordance with another aspect of the present invention, also provided is a preparation method for the valve described above. The preparation method includes: placing an insert into the mold cavity of the injection mold of the valve, molding the mold core with the mold cavity to form an injection cavity containing the insert; injecting a polymer material in a molten state into the injection cavity, waiting for the polymer material in the injection cavity to cool to below the glass transition temperature, opening the injection mold to obtain a one-time molded valve containing the insert.

Optionally, it includes: heating the injection mold to 80-100° C., heating the polymer material to a molten state of 280-300° C., and injecting into the injection cavity of the injection mold at a rate of 0.3-1 $cm^3/s$ under an injection pressure of 50 MPa;

when the polymer material is filled to 85%-98% of the injection cavity, changing the injection pressure to 30 MPa and maintaining for 3-6 s until the filling is completed;

cooling the injection mold to 30-50° C. at a cooling rate of 15-20° C./min such that the polymer material cools below a glass transition temperature, the glass transition temperature being 85° C.; and opening the injection mold and removing the one-time molded valve containing the insert from the injection mold.

Optionally, the insert includes an axial positioning structure and a radial positioning structure. The axial positioning structure includes positioning peaks arranged at the third end and corresponding to the column peaks in the circumferential direction. The positioning peak is symmetrically provided on both sides with positioning grooves and formed with positioning side peaks at edges of the positioning peak. The axial positioning structure further includes a plurality of sets of positioning teeth arranged at intervals. The positioning teeth are provided at the fourth end. The circumferential positions of the plurality of sets of the positioning teeth correspond to the column peaks and the column valleys on a one-to-one basis. Each set of positioning teeth includes two teeth. The radial positioning structure includes positioning protrusions provided on the outer wall of the insert. The apexes of the positioning protrusions abut to an inner wall of the mold cavity. The operation method further includes: placing the insert in the mold cavity according to the axial positioning of the positioning peaks, the positioning side peaks, and the positioning teeth, and the radial positioning of the positioning protrusions.

Optionally, the cavity is provided with injection holes. The injection holes are arranged in correspondence to the first end of the valve frame. The number of the injection holes is plural, and the plurality of the injection holes are provided in correspondence with the column peaks on a one-to-one basis. The operation method further includes: injecting a polymer material in a molten state into the injection cavity from the injection holes.

Compared with the prior art, the technical solution of the embodiments of the present invention has beneficial effects.

For example, the insert is embedded in the valve frame to improve the radial support force of the valve frame; one-time injection molding of the valve frame and valve leaflets is adopted to optimize the valve performance, avoid using different materials for the valve frame and valve leaflets, resulting in poor bonding between the valve frame and valve leaflets, avoiding two-time injection of the valve frame and valve leaflets, so that the preparation process is simplified and the preparation efficiency is improved.

For another example, by setting a positioning structure on the insert, the displacement of the insert caused by injection pressure during injection molding can be avoided. At the same time, the thickness from the inner and outer walls of the valve frame to the insert can be uniform, resulting in better wrapping performance.

For another example, the injection hole is provided on the valve frame to avoid the influence on the valve leaflet by the fracture trace generated when the polymer material injected into the channel is separated from the valve leaflets.

DESCRIPTION OF REFERENCE NUMERALS

Figure 1:
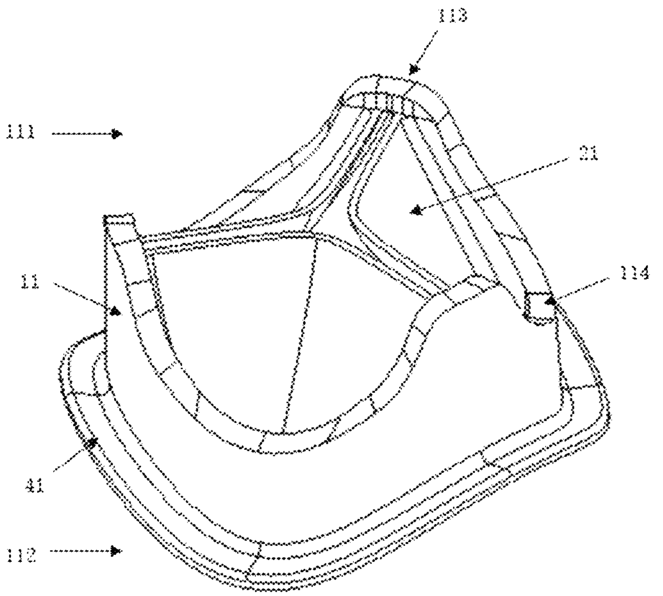
FIG. 1 is a structural schematic diagram of a polymeric heart valve in an embodiment of the present invention.
Figure 2:
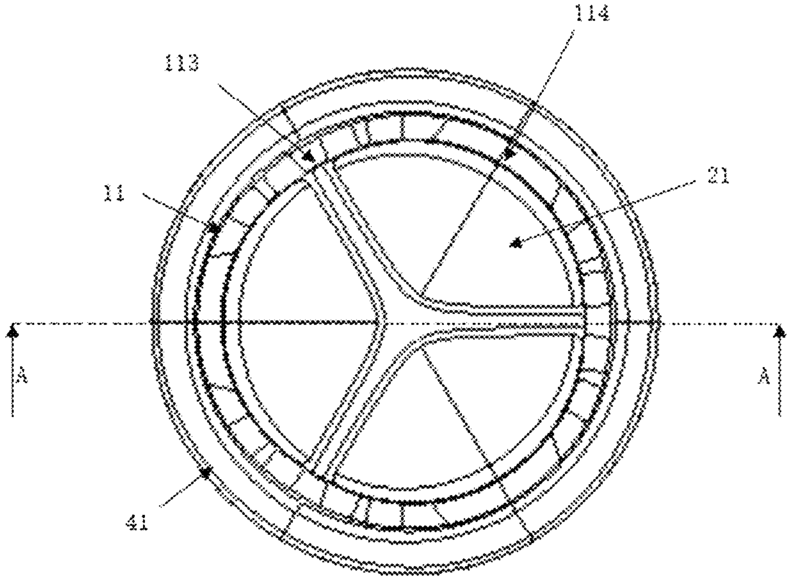
FIG. 2 is a top view of a polymeric heart valve according to an embodiment of the present invention.

11, valve frame; 111, first end; 112, second end; 113, column peak; 114, column valley;

21, valve leaflet;

31, insert; 311 third end, 312, fourth end; 313, lightening hole; 314, positioning peak;

315, positioning groove; 316, positioning tooth; 3161, tooth; 317, positioning protrusion;

318, positioning side peak;

41, annular edge;

51, mold cavity; 511, injection hole;

61, mold core; and

71, injection cavity.

DETAILED DESCRIPTION OF THE INVENTION

In order to make the purpose, features, and beneficial effects of the present invention more obvious and understandable, the detailed embodiments of the present invention will be described in detail below in conjunction with the accompanying drawings. It can be understood that the specific embodiments described below are only used to explain the present invention, and not to limit the present invention. Also, the same or similar reference numerals may be used in the drawings to refer to the same or similar elements in different embodiments, and descriptions of the same or similar elements in different embodiments and descriptions of elements, features, effects, etc. of the prior art may be omitted. It should be noted that the axial, radial, and circumferential directions described for the embodiments of the present invention refer to the axial, radial, and circumferential directions of the valve frame 11, respectively.

Referring to FIGS. 1-5, embodiments of the present invention provide a polymeric heart valve.

In a specific implementation, a polymeric heart valve includes a valve leaflet 21 and a valve frame 11. The valve frame 11 is a hollow cylindrical structure and includes a first end 111 and a second end 112. The first end 111 is provided with a plurality of column peaks 113 arranged at intervals in the circumferential direction, and column valleys 114 are correspondingly formed. The number of valve leaflets 21 is consistent with the number of column peaks 113. The valve leaflets 21 are arranged in the center of the first end 111. A plurality of the valve leaflets 21 sequentially connected to two adjacent column peaks 113 in the circumferential direction. The valve further includes an insert 31. The insert 31 is a hollow cylindrical structure matching the valve frame 11. The insert 31 includes a third end 311 and a fourth end 312 corresponding to the first end 111 and the second end 112, respectively. The insert 31 is suitable for being embedded in the valve frame 11 in the axial direction. The valve leaflets 21 and the valve frame 11 are subjected to one-time injection molding. The insert 31 is embedded into the valve frame 11 to become a whole when the valve frame 11 and the valve leaflets 21 are subjected to injection molding.

In a specific implementation, the number of the valve leaflets 21 and the number of the column peaks 113 are both three. When the blood flows from the first end 111 to the second end 112, the valve leaflets 21 are closed to prevent the blood from flowing. As blood passes from the second end 112 to the first end 111, the valve leaflets 21 are open to allow blood to pass therethrough.

In some embodiments, the number of the valve leaflets 21 and the number of column peaks 113 are both two.

In some embodiments, the number of the valve leaflets 21 may be selected based on the location of the application.

In some embodiments, the second end 112 is provided with an annular edge 41.

In a specific implementation, the valve leaflets 21 and the valve frames 11 are made of a polymer material and the insert 31 is made of a hard material. The hard material refers to the composite material, non-metallic material, and hard alloy with surface hardness reaching HRC22. The valve frame 11 completely wraps insert 31 so that insert 31 may be metallic or non-metallic.

Since the valve frame 11 and valve leaflets 21 of polymer material are relatively soft and the radial support force of the entire valve is insufficient, it is necessary to implant an insert 31 within the valve frame 11 to increase the radial support force. The insert 31 needs to withstand the pressure exerted on it by the polymer material during injection molding, withstand the high temperature exerted on it by the molten polymers and meet the biocompatibility requirements for long-term implantation in the human body.

Figure 3:
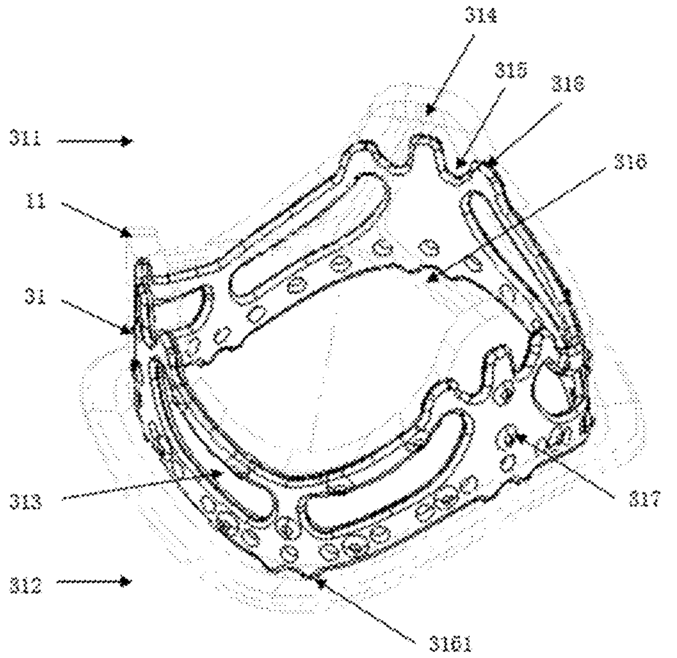
FIG. 3 is a structural schematic diagram of an insert in an embodiment of the present invention.
Figure 4:
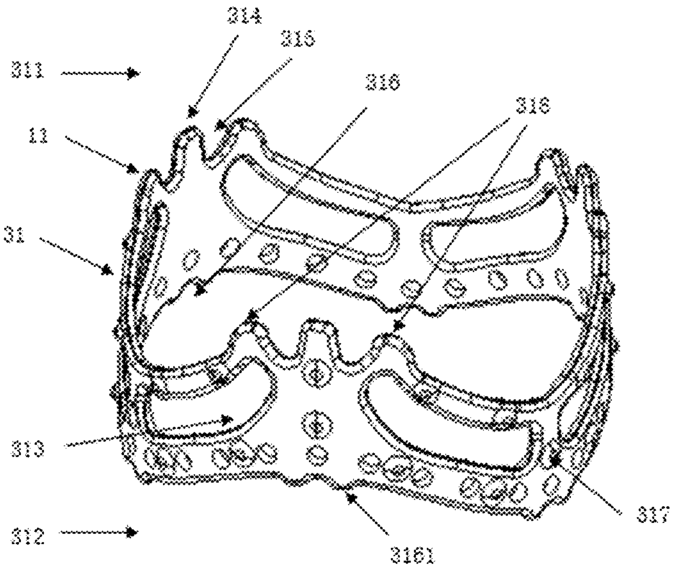
FIG. 4 is a structural schematic diagram of the insert from another view in an embodiment of the present invention.

Referring to FIGS. 3 and 4, in a specific implementation, the insert 31 includes an axial positioning structure and a radial positioning structure 317. The axial positioning structure includes positioning peaks 314, wherein the positioning peaks 314 are arranged at the third end 311 and are at the same positions as the column peaks 113 in the circumferential direction. The positioning peak 314 is symmetrically provided on both sides with positioning grooves 315 and formed with positioning side peaks 318 at the edges of the positioning peak 314. The positioning side peak 318 realizes the axial and circumferential positioning of the insert 31, so as to avoid the axial displacement or circumferential displacement of the insert 31 during injection molding due to the injection molding pressure. The positioning groove 315 increases the wrapping area around the insert 31, realizing a better wrapping effect, so as to avoid the insert 31 separating from the valve frame 11. At the same time, the use of the material of the insert 31 is reduced, saving raw materials.

In some embodiments, the axial positioning structure further includes a plurality of sets of positioning teeth 316 arranged at intervals. The positioning teeth 316 are provided at the fourth end 312. The circumferential positions of the plurality of sets of the positioning teeth 316 are the same as the positions of the column peaks 113 and column valleys 114. Each set of positioning teeth 316 includes two teeth 3161. The positioning teeth 316 mate with positioning side peaks 318 for further accurate positioning.

Figure 5:
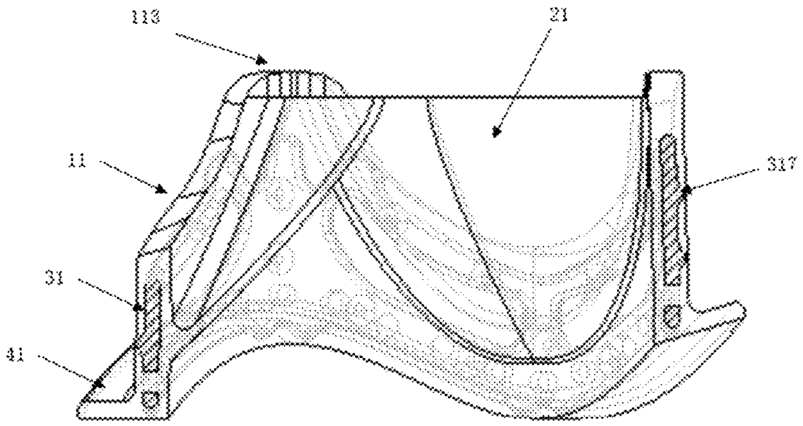
FIG. 5 is a cross-sectional view of AA in FIG. 2.

Referring to FIG. 5, in a specific implementation, the radial positioning structure 317 includes positioning protrusions 317 arranged on the outer wall of the insert 31. The positioning protrusions 317 are uniformly arranged on the outer wall of the insert 31. The positioning protrusion 317 provides radial positioning of the insert 31, preventing radial displacement of the insert 31 during injection molding due to injection pressure. In a specific implementation, the positioning protrusion 317 may be provided in a circular shape or other shapes that facilitate fabrication.

In some embodiments, the insert 31 is provided with a plurality of lightening holes 313. The plurality of lightening holes 313 are arranged at intervals in the circumferential direction. The lightening holes 313 are arranged between adjacent column peaks 113 and column valleys 114. Without affecting the supporting force of the insert 31, the use of the material of the insert 31 is minimized to save raw materials. At the same time, the wrapping area around the insert 31 is increased, so that the wrapping effect is better and the insert 31 is prevented from escaping from the valve frame 11.

Figure 6:
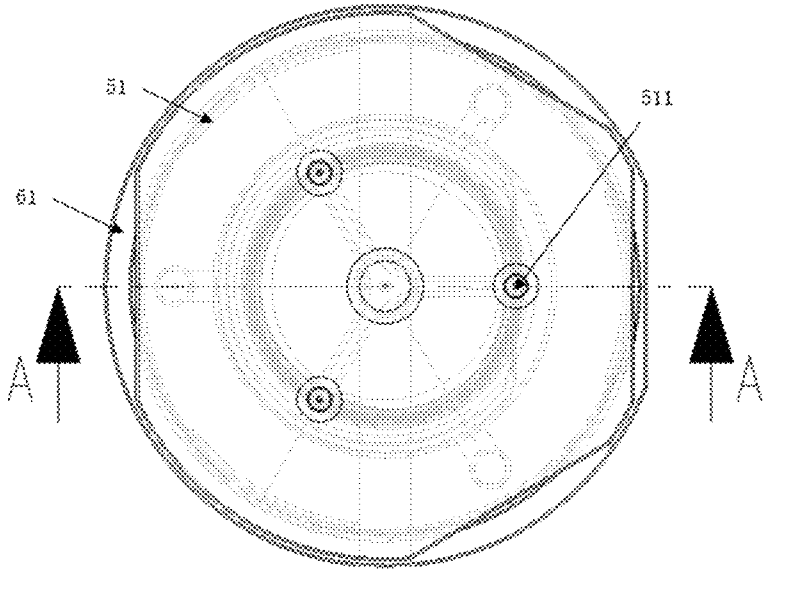
FIG. 6 is a top view of an injection mold in an embodiment of the present invention.
Figure 7:
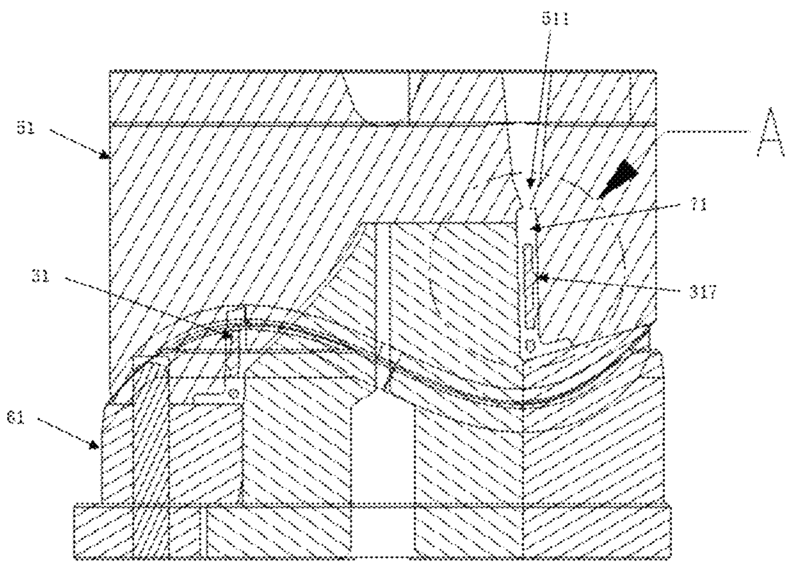
FIG. 7 is a cross-sectional view of AA in FIG. 6.
Figure 8:
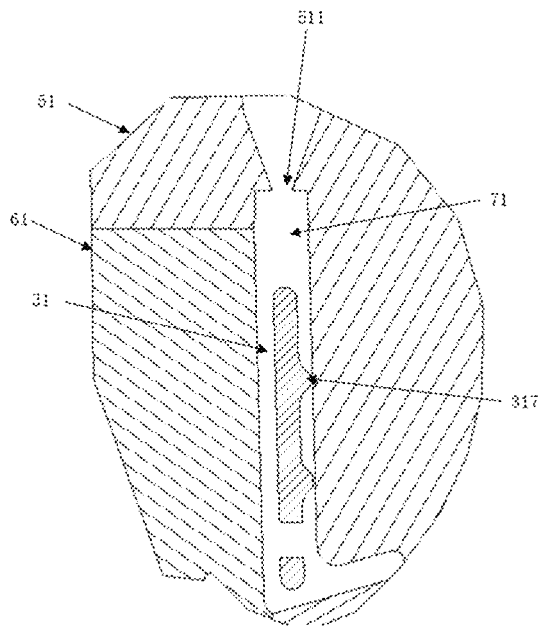
FIG. 8 is an enlarged partial view of point A in FIG. 7.

With reference to FIGS. 6-8, in a specific implementation, when the valve frame 11 and the valve leaflets 21 are subjected to one-time injection molding, the insert 31 is arranged in an injection cavity 71 formed by an injection mold. The injection mold includes a mold cavity 51 and a mold core 61. The outer wall of the mold core 61 mates with the inner wall of the mold cavity 51 to form the injection cavity 71. The apexes of the positioning protrusions 317 abut to the inner wall of the mold cavity 51 so that the distance between the outer wall of the insert 31 and the inner wall of the mold cavity 51 is equal to the distance between the inner wall of the insert 31 and the outer wall of the mold core 61. That is to say, the thickness from the inner wall and the outer wall of the valve frame 11 to the insert 31 is uniform, and the coating performance is better, and the insert 31 is not easily dislodged from the valve frame 11.

Figure 9:
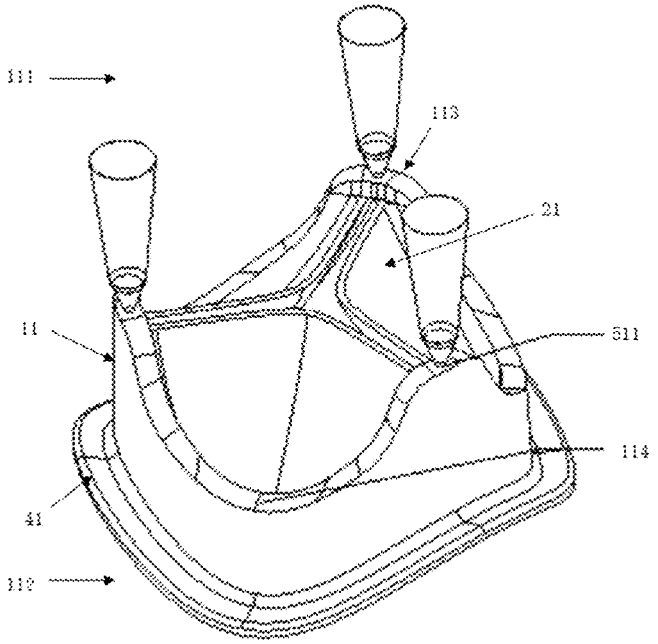
FIG. 9 is a view showing the layout of injection holes of a polymeric heart valve in an embodiment of the present invention.

Referring also to FIG. 9, in a specific implementation, the mold cavity 51 is provided with injection holes 511 that are arranged in correspondence with the end surface of the first end 111 of the valve frame 11. At the same time, due to the greater thickness of the polymer material at the valve frame 11, it is not easy to form a fracture trace on the surface of the valve frame 11 when the polymer material at the injection hole 511 breaks, and the valve frame 11 plays a supporting role and does not move when in use so that the fracture trace has less effect on the valve frame 11. Compared with the prior art, it is easy to form a fracture trace by arranging the injection hole 511 at the center of the valve leaflets 21, and it is easy to form a crack at the fracture trace due to the opening and closing of the valve leaflets 21 when in use. The valve performance can be optimized by changing the position of the injection hole 511.

In a specific implementation, the number of the injection holes 511 is plural, and the plurality of the injection holes 511 are provided in correspondence with the column peaks 113 on a one-to-one basis. The column peak 113 of the valve frame 11 has the greatest thickness and highest location of polymer material, which facilitates the flow of polymer material during injection filling. In some embodiments, the injection holes 511 may also be provided at the column valleys 114.

In some embodiments, the center of the valve leaflets 21 is provided with a gas-permeable groove. The gas-permeable groove in the center of the valve leaflets 21 is more conducive to the flow of polymer material at the valve leaflet 21 during injection molding. The diameter of the air-permeable groove is 0.005 mm-0.01 mm. When the diameter is greater than 0.01 mm, the polymer material may overflow, forming a rough edge on the surface of the valve leaflets 21. A diameter of less than 0.005 mm hinders venting and affects the flow of the polymer material.

In order to facilitate an understanding of the technical solution of the polymeric heart valve provided in the embodiments of the present invention, a preparation method for the heart valve is described.

In some embodiments, the preparation method may include the following steps:

S1: placing the insert 31 in the mold cavity 51 according to the axial and circumferential positioning of the positioning peaks 314 and the positioning teeth 316 and the radial positioning of the positioning protrusions 317;

S2: molding the mold core 61 with the mold cavity 51 to form an injection cavity 71 containing the insert 31;

S3: heating the injection mold to 80-100° C., preferably to 90° C.; heating the polymer material to a molten state of 280-300° C., preferably at a temperature of 290° C.; and injecting into the injection cavity 71 of the injection mold at a rate of 0.3-1 $cm^3$/s, preferably at a rate of 0.5 $cm^3$/s, under an injection pressure of 50 MPa;

S4: when the polymer material is filled to 85%-98% of the injection cavity 71, changing the injection pressure to 30 MPa and maintaining for 3-6 s, preferably for 4.5 s, until the filling is completed;

S5: cooling the injection mold to 30-50° C., preferably 40° C., at a cooling rate of 15-20° C./min, such that the polymer material cools below a glass transition temperature, the glass transition temperature being 85° C.;

S6: opening the injection mold and removing the one-time molded valve containing the insert 31 from the injection mold.

While specific embodiments have been described above, these embodiments are not intended to limit the scope of the disclosure, even if a single embodiment is described with respect to only certain features. The examples of features provided in this disclosure are intended to be illustrative, and not limiting, unless expressed differently. In a specific implementation, the technical features of one or more dependent claims can be combined with the technical features of independent claims as technically feasible according to actual needs, and the technical features from the corresponding independent claims can be combined in any appropriate way rather than just through specific combinations listed in the claims.

Although the present invention is disclosed above, the present invention is not limited thereto. Various changes and modifications may be made by one skilled in the art without departing from the spirit and scope of the present invention, which is intended to be limited only by the scope of the appended claims.

What is claimed is:

1. A polymeric heart valve comprising a valve leaflet and a valve frame, wherein the valve frame is a hollow cylindrical structure and comprises a first end and a second end; the first end is provided with a plurality of column peaks arranged at intervals in the circumferential direction, and column valleys are correspondingly formed; the number of the valve leaflets is consistent with the number of the column peaks; the valve leaflets are arranged in the center of the first end; a plurality of the valve leaflets sequentially connected to two adjacent column peaks in the circumferential direction; the valve further comprises an insert; the insert is a hollow cylindrical structure matching the valve frame; and the insert comprises a third end and a fourth end corresponding to the first end and the second end, respectively; the insert is suitable for being embedded in the valve frame in the axial direction; the insert comprises an axial positioning structure and a radial positioning structure; the valve leaflets and the valve frame are subjected to one-time injection molding; the insert is embedded into the valve frame to become a whole when the valve frame and the valve leaflets are subjected to injection molding; the radial positioning structure comprises positioning protrusions arranged on the outer wall of the insert; and the positioning protrusions are uniformly arranged on the outer wall of the insert, and wherein a center of the valve leaflets is provided with a gas-permeable groove having a diameter of 0.005 mm-0.01 mm.

2. The polymeric heart valve according to claim 1, wherein the axial positioning structure comprises positioning peaks arranged at the third end and corresponding to the column peaks in the circumferential direction; the positioning peak is symmetrically provided on both sides with positioning grooves and formed with positioning side peaks at edges of the positioning peak.

3. The polymeric heart valve according to claim 1, wherein the axial positioning structure further comprises a plurality of sets of positioning teeth arranged at intervals; the positioning teeth are provided at the fourth end; the circumferential positions of the plurality of sets of the positioning teeth correspond to the column peaks and the column valleys on a one-to-one basis; and each set of positioning teeth comprises two teeth.

4. The polymeric heart valve according to claim 1, wherein the insert is provided with a plurality of lightening holes; the plurality of lightening holes is arranged at intervals in a circumferential direction; and the lightening holes are respectively arranged between the adjacent column peaks and column valleys.

5. The polymeric heart valve according to claim 1, wherein the second end is provided with an annular edge.

6. The polymeric heart valve according to claim 1, wherein the valve leaflets and the valve frame are made of a polymer material and the insert is made of a hard material.

* * * * *